United States Patent
Matsuhama et al.

(10) Patent No.: US 11,949,210 B2
(45) Date of Patent: Apr. 2, 2024

(54) SEMICONDUCTOR LASER DEVICE AND ANALYSIS APPARATUS

(71) Applicant: HORIBA, LTD., Kyoto (JP)

(72) Inventors: Makoto Matsuhama, Kyoto (JP); Yusuke Awane, Kyoto (JP); Kimihiko Arimoto, Kyoto (JP); Hirotaka Iseki, Kyoto (JP); Shintaro Masuda, Kyoto (JP)

(73) Assignee: Horiba, Ltd. (JP)

( * ) Notice: Subject to any disclaimer, the term of this patent is extended or adjusted under 35 U.S.C. 154(b) by 403 days.

(21) Appl. No.: 16/811,710

(22) Filed: Mar. 6, 2020

(65) Prior Publication Data
US 2020/0287349 A1    Sep. 10, 2020

(30) Foreign Application Priority Data

Mar. 8, 2019    (JP) .................................. 2019-043099

(51) Int. Cl.
*H01S 5/024* (2006.01)
*G01N 33/00* (2006.01)
(Continued)

(52) U.S. Cl.
CPC ..... *H01S 5/02415* (2013.01); *G01N 33/0009* (2013.01); *H01S 5/02325* (2021.01);
(Continued)

(58) Field of Classification Search
CPC .................................................. H01S 5/02446
See application file for complete search history.

(56) References Cited

U.S. PATENT DOCUMENTS 6,487,027 B2 * 11/2002 Yamauchi ........... H01S 5/02415
                                                                    372/32
6,490,303 B1 * 12/2002 Komiyama ......... H01S 5/02216
                                                                    359/819
(Continued)

FOREIGN PATENT DOCUMENTS

CN       104332524 A  *  2/2015  ............. G01S 17/04
CN       106797104 A  *  5/2017  ........... H01L 23/045
(Continued)

OTHER PUBLICATIONS

EESR dated Jul. 10, 2020 issued for European Patent Application No. 20160970.8, 6 pgs.
(Continued)

*Primary Examiner* — Tod T Van Roy
(74) *Attorney, Agent, or Firm* — Brooks Kushman P.C.

(57) ABSTRACT

The present invention relates to a semiconductor laser device capable of reducing a measurement error of a temperature detecting element for detecting the temperature of a semiconductor laser element and accurately controlling the temperature of the semiconductor laser element. The semiconductor laser device is used for optical analysis and includes: a semiconductor laser element; a temperature detecting element that detects the temperature of the semiconductor laser element; output terminals that output the output of the temperature detecting element to the outside; wires that electrically connect the temperature detecting element and the output terminals; and a heat capacity increasing part that is provided interposed between the temperature detecting element and output terminal, and the output terminal, and contacts with at least part of the wires to increase the heat capacity of the wires.

5 Claims, 7 Drawing Sheets

(51) Int. Cl.
*H01S 5/02325* (2021.01)
*H01S 5/02345* (2021.01)
*H01S 5/028* (2006.01)
*H01S 5/12* (2021.01)
*H01S 5/34* (2006.01)
*H01S 5/02216* (2021.01)

(52) U.S. Cl.
CPC ...... *H01S 5/02345* (2021.01); *H01S 5/02438* (2013.01); *H01S 5/02446* (2013.01); *H01S 5/028* (2013.01); *H01S 5/12* (2013.01); *H01S 5/3402* (2013.01); *H01S 5/02216* (2013.01)

(56) References Cited

U.S. PATENT DOCUMENTS

| | | | | |
|---|---|---|---|---|
| 6,543,102 B1* | 4/2003 | Zitzmann | G01F 1/6845 | 374/E7.022 |
| 6,740,963 B2* | 5/2004 | Kaneko | H01S 5/042 | 372/36 |
| 7,280,181 B2* | 10/2007 | Finot | G02B 6/4201 | 349/200 |
| 7,366,367 B2* | 4/2008 | Kuhara | G02B 6/4202 | 385/88 |
| 7,403,347 B2* | 7/2008 | Ueki | G02B 6/4204 | 372/36 |
| 7,856,038 B2* | 12/2010 | Oomori | H01S 5/023 | 372/36 |
| 7,869,476 B2* | 1/2011 | Kamijima | H01S 5/14 | 372/33 |
| 8,320,763 B2* | 11/2012 | Kim | H01S 5/0612 | 398/68 |
| 8,909,010 B2* | 12/2014 | Kimura | H01S 5/02251 | 385/94 |
| 9,007,136 B2 | 4/2015 | Chindo | | |
| 9,515,454 B2* | 12/2016 | Kim | H01S 5/0687 | |
| 10,001,590 B2* | 6/2018 | Hasegawa | G02B 6/4286 | |
| 10,096,970 B2* | 10/2018 | Maki | H01S 5/02257 | |
| 10,184,652 B2* | 1/2019 | Ichikawa | H01S 5/0087 | |
| 10,224,692 B2* | 3/2019 | Onishi | H01S 5/18344 | |
| 10,431,955 B2* | 10/2019 | Serbicki | H01S 5/3402 | |
| 11,011,886 B2* | 5/2021 | Gelhausen | H01S 5/0233 | |
| 11,043,790 B2* | 6/2021 | Tokuda | H01S 5/0286 | |
| 2001/0033592 A1 | 10/2001 | Yamauchi et al. | | |
| 2003/0001081 A1* | 1/2003 | Kaneko | H01S 5/02345 | 250/216 |
| 2005/0117231 A1 | 6/2005 | Ueki et al. | | |
| 2007/0002927 A1* | 1/2007 | Finot | H01S 5/02438 | 372/99 |
| 2010/0177793 A1 | 7/2010 | Rossi et al. | | |
| 2011/0110390 A1* | 5/2011 | Willing | G01N 21/39 | 372/50.23 |
| 2014/0293287 A1 | 10/2014 | Hirao | | |
| 2015/0000395 A1* | 1/2015 | Tashiro | G01F 1/6842 | 73/204.26 |
| 2015/0200730 A1* | 7/2015 | Kim | H01S 5/0687 | 372/20 |
| 2016/0061653 A1* | 3/2016 | Chang | H01S 25/167 | 250/237 R |
| 2016/0301187 A1 | 10/2016 | Weida et al. | | |
| 2018/0337319 A1* | 11/2018 | Migita | H01L 35/32 | |
| 2019/0305787 A1* | 10/2019 | Hagino | H03L 7/26 | |
| 2020/0287349 A1* | 9/2020 | Matsuhama | H01S 5/028 | |
| 2021/0013698 A1* | 1/2021 | Kasai | H01S 5/0021 | |
| 2021/0098964 A1* | 4/2021 | Kim | H01S 5/02325 | |
| 2021/0159664 A1* | 5/2021 | Liu | H01S 5/02253 | |
| 2022/0360039 A1* | 11/2022 | Russell | H01S 5/4056 | |

FOREIGN PATENT DOCUMENTS

| | | | | |
|---|---|---|---|---|
| EP | 0664586 A | 7/1995 | | |
| EP | 1602952 A | 12/2005 | | |
| EP | 2793329 A1 | 10/2014 | | |
| EP | 3243205 B1 * | 4/2019 | | C08J 3/24 |
| JP | S6212174 A | 1/1987 | | |
| JP | S6213088 A | 1/1987 | | |
| JP | 2001-184694 A | 7/2001 | | |
| JP | 2001-296173 A | 10/2001 | | |
| JP | 2003-133633 A | 5/2003 | | |
| JP | 2004-282027 A | 10/2004 | | |
| JP | 2009-264975 A | 11/2009 | | |
| JP | 2010-287596 A | 12/2010 | | |
| JP | 5598386 B2 * | 10/2014 | | H01L 24/33 |
| JP | 2015005566 A * | 1/2015 | | H01L 24/32 |
| JP | 2015-119152 A | 6/2015 | | |
| JP | 2018-194423 A | 12/2018 | | |
| WO | WO-2006032726 A1 * | 3/2006 | | G02B 6/4206 |
| WO | 2013084746 A1 | 4/2015 | | |
| WO | WO2016/110570 A | 7/2016 | | |
| WO | WO-2020024240 A1 * | 2/2020 | | H01S 5/02253 |

OTHER PUBLICATIONS

Office Action dated Nov. 25, 2021 issued in JP patent application No. 2019-043099, 9 pgs.

Office Action dated May 16, 2023 issued in EP patent application No. 20160970.8.

* cited by examiner

SEMICONDUCTOR LASER DEVICE AND ANALYSIS APPARATUS

CROSS-REFERENCE TO RELATED APPLICATION

[0001] This application claims priority to Japanese Application No. 2019-043099, filed Mar. 8, 2019, the disclosure of which is incorporated in its entirety by reference herein.

TECHNICAL FIELD

The present invention relates to a semiconductor laser device and analysis apparatus used for optical analysis.

BACKGROUND ART

Usually, for example, in a gas analysis apparatus using a semiconductor laser element, a variation in the wavelength of laser light emitted from the semiconductor laser element affects analysis accuracy, and therefore the temperature of the semiconductor laser element as one of the factors of the variation in the wavelength is controlled to a desired temperature.

For example, in Patent Literature 1, a temperature control part including a Peltier element, a supporting substrate, and the like is mounted with a semiconductor laser element and a temperature detection part such as a thermistor to control the temperature control part on the basis of temperature obtained by the temperature detection part. In doing so, the temperature of the semiconductor laser element is controlled to a desired temperature to suppress a variation in the wavelength of laser light. A semiconductor laser light source in Patent Literature 1 includes the semiconductor laser element, the temperature detection part, the temperature control part in an internal space formed by a base member and a cap member. In addition, multiple pin terminals provided penetrating through the base member from outside the base member toward the internal space are electrically connected to the semiconductor laser element, temperature detection part, and temperature control part by electrically conductive wires.

However, along with a change in the ambient temperature of the semiconductor laser light source, the temperature of the pin terminals provided to the base member changes, and heat is transferred to the temperature detection part from pin terminals through electrically conductive wires. This causes the temperature of the temperature detection part to be varied by the heat from the electrically conductive wires. As a result, a measurement error occurs in the temperature of the semiconductor laser element, making it difficult to accurately control the temperature of the semiconductor laser element.

CITATION LIST

Patent Literatures

Patent Literature 1: International Publication No. 2013/084746

SUMMARY OF INVENTION

Technical Problem

Therefore, the present invention has been made in order to solve the above-described problem, and the main object thereof is to make it possible to accurately control the temperature of a semiconductor laser element by reducing a measurement error of a temperature detecting element for detecting the temperature of the semiconductor laser element.

Solution to Problem

That is, the semiconductor laser device according to the present invention is one used for optical analysis, and the semiconductor laser device includes: a semiconductor laser element; a temperature detecting element that detects the temperature of the semiconductor laser element; an output terminal that outputs the output of the temperature detecting element to the outside; a wire that electrically connects the temperature detecting element and the output terminal; and a heat capacity increasing part that is provided interposed between the temperature detecting element and the output terminal and contacts with at least a part of the wire to increase the heat capacity of the wire.

Such a semiconductor laser device is capable of reducing the amount of heat transferring through the wire and flowing into the temperature detecting element because there is provided the heat capacity increasing part that contacts with the wire connecting the temperature detecting element and the output terminal to increase the heat capacity of the wire. As a result, the temperature of the semiconductor laser element can be accurately detected by the temperature detecting element, making it possible to highly accurately control the temperature of the semiconductor laser element.

In order to preferably use the semiconductor laser element for optical analysis such as infrared spectroscopic analysis, the semiconductor laser element is desirably a quantum cascade laser. The quantum cascade laser requires large power consumption by one or more orders of magnitude as compared with normal semiconductor lasers and easily causes a temperature change, and is therefore significantly affected by wavenumber variation. According to the present invention, since the temperature of a quantum cascade laser can be highly accurately controlled, wavenumber variation due to a temperature change can be suppressed, making it possible to highly accurately perform the optical analysis.

As a specific embodiment for adjusting the temperature of the semiconductor laser element, it is desirably that the semiconductor laser device further includes: a cooling mechanism that is mounted with the semiconductor laser element and for cooling the semiconductor laser element; and a control part that uses the detected temperature by the temperature detecting element to control the cooling mechanism.

When directly mounting the semiconductor laser element on the cooling mechanism, the difference in thermal expansion coefficient between the cooling mechanism and the semiconductor laser element may cause strain in both or causes a gap between both to prevent heat transfer.

For this reason, it is conceivable that the semiconductor laser device further includes a sub-mount that is provided interposed between the cooling mechanism and the semiconductor laser element. It is also conceivable to set the thermal expansion coefficient of the sub-mount between the thermal expansion coefficient of the cooling mechanism and that of the semiconductor laser element. In addition, as the material of the sub-mount, it is conceivable to use ceramic such as aluminum nitride (AlN) or silicon carbide (SiC).

In order to increase the heat capacity of the wire and also positively make the temperature of the wire equal to that of the semiconductor laser element, it is desirable that the heat capacity increasing part is in contact with the sub-mount. In this case, by configuring the heat capacity increasing part to cover part of the wire, the volume of the heat capacity increasing part can be decreased as compared with a configuration in which the wire is entirely covered, and therefore temperature adjustment based on heat transfer from the sub-mount can be facilitated to shorten a time required for stabilizing the temperature of the wire (e.g., a warming-up time).

It is desirable that the heat capacity increasing part is formed of silicone that is an insulating material. In this configuration, the heat capacity can be increased without preventing an electrical signal from being transmitted through the wire. Also, since silicone has flexibility, the wire becomes unlikely to be broken, and the heat capacity increasing part also plays a role in protecting the wire.

In order to configure the heat capacity increasing part using an existing configuration, it is desirable that the wire is embedded in the sub-mount, and the sub-mount functions as the heat capacity increasing part.

In addition, it is desirable that the sub-mount is a multilayer ceramic substrate, and the wire is configured using a wire in the multilayer ceramic substrate.

Light may leak out of an end surface on the side opposite to the light emitting surface of the semiconductor laser element and the light leaking out may serve as stray light. Therefore, in order to reduce the stray light, it is desirable that the semiconductor laser device further includes a light shielding part that faces the end surface on the side opposite to the light emitting surface of the semiconductor laser element to shield the light coming out of the end surface.

Also the temperature detecting element is provided facing the end surface on the side opposite to the light emitting surface of the semiconductor laser element, and thereby the stray light can be reduced by the temperature detecting element.

Also, the analysis apparatus according to the present invention is one that analyzes a measurement target component contained in fluid, and the analysis apparatus includes: a measurement cell into which the fluid is introduced; the above-described semiconductor laser device that irradiates the measurement cell with laser light; a light detector that detects laser light passing through the measurement cell; and an analysis part that uses a detected signal by the light detector to analyze the measurement target component.

Such an analysis apparatus can highly accurately control the temperature of the semiconductor laser element, and therefore accurately analyze the measurement target component contained in the fluid.

Advantageous Effects of Invention

According to the present invention configured as described, a measurement error of the temperature detecting element that detects the temperature of the semiconductor laser element can be reduced, making it possible to accurately control the temperature of the semiconductor laser element.

DESCRIPTION OF EMBODIMENTS

In the following, one embodiment of the semiconductor laser device according to the present invention will be described with reference to the drawings.

Figure 1:
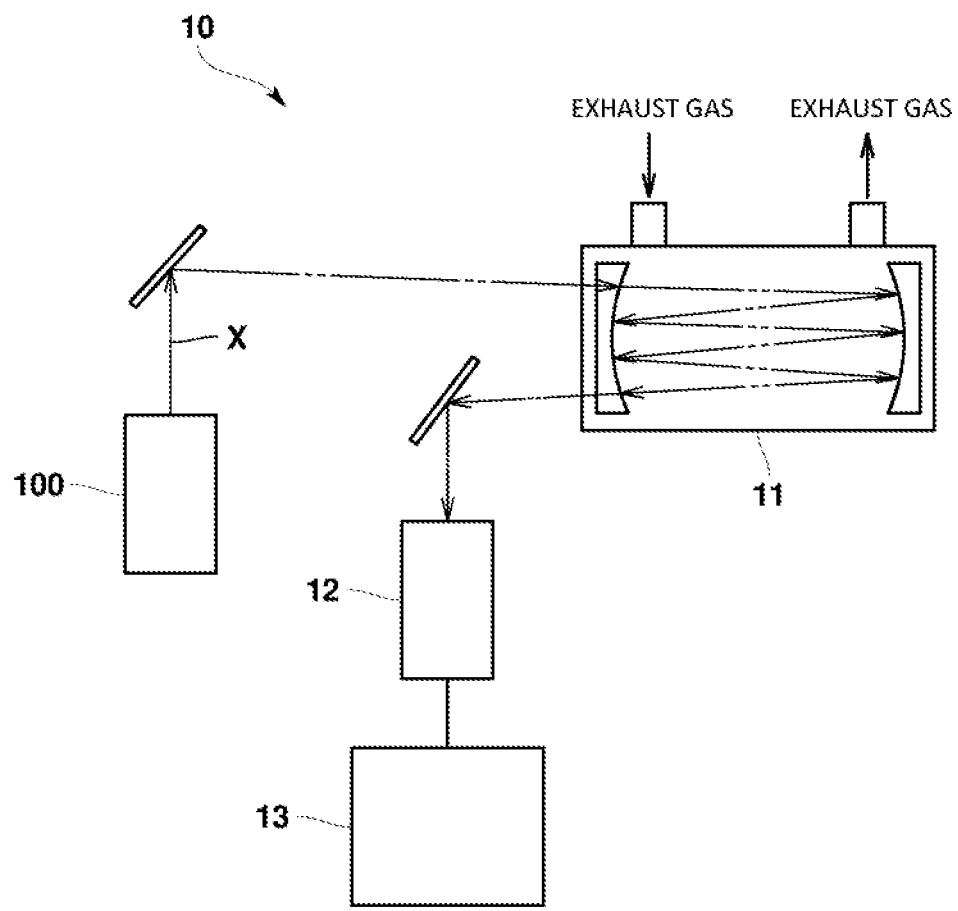
FIG. 1 is an overall schematic view of an exhaust gas analysis apparatus using a semiconductor laser device according to the present embodiment.

As illustrated in FIG. 1, a semiconductor laser device 100 of the present embodiment is one used for, for example, an exhaust gas analysis apparatus 10 that analyzes a measurement target components (e.g., CO, $CO_2$, $H_2O$, NO, $NO_2$, $N_2O$, $NH_3$, a hydrocarbon component such as HC, or an oxygen-containing hydrocarbon component such as HCHO) in exhaust gas discharged from an internal combustion engine. The exhaust gas analysis apparatus 10 includes: a multireflection measurement cell 11 into which the exhaust gas is introduced; the semiconductor laser device 100 that irradiates the measurement cell 11 with laser light X; a light detector 12 that detects laser light X passing through the measurement cell 11; and an analysis part 13 that analyzes the measurement target component using a detected signal by the light detector 12. Note that the measurement cell 11 is not limited to the multireflection measurement cell but may be a single reflection measurement cell or a one-pass measurement cell not using reflection.

Figure 2:
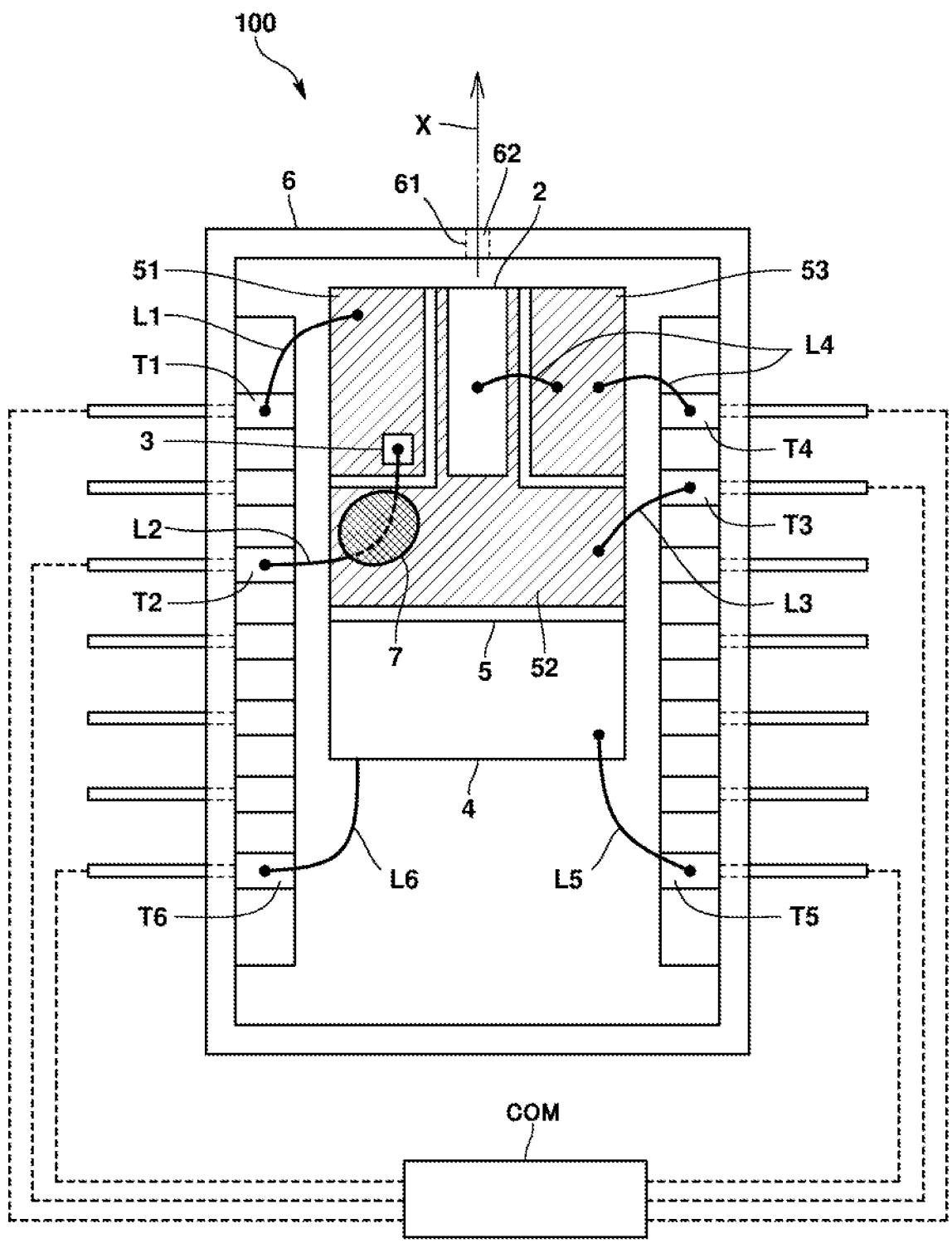
FIG. 2 is a plan view schematically illustrating the overall configuration of the semiconductor laser device according to the same embodiment.
Figure 3:
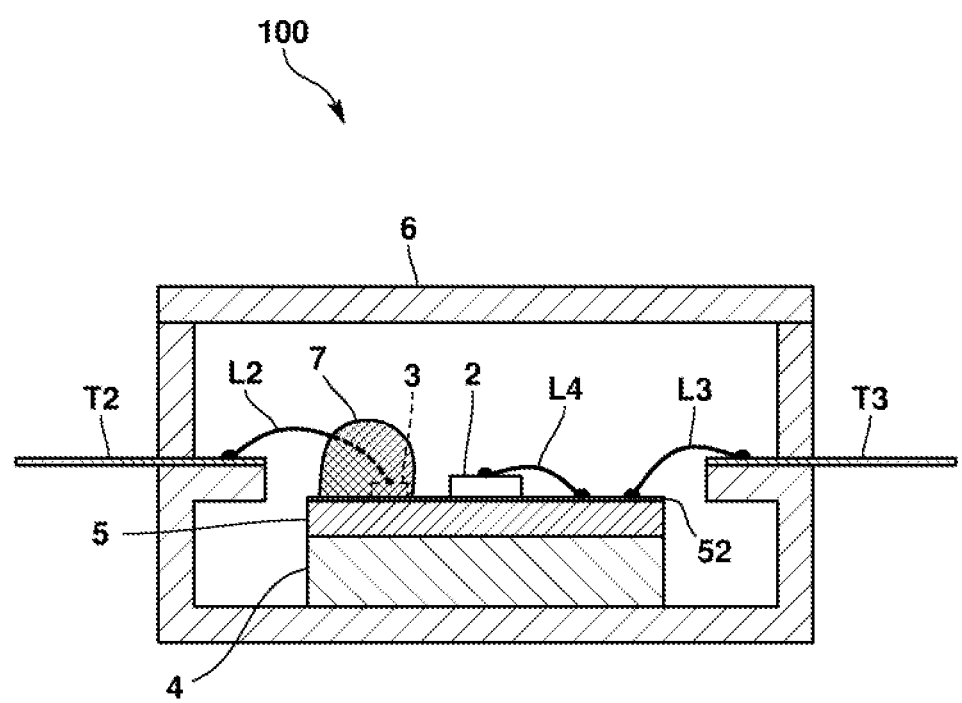
FIG. 3 is a cross-sectional view schematically illustrating the overall configuration of the semiconductor laser device according to the same embodiment.

Specifically, the semiconductor laser device 100 is one that emits the laser light X having oscillation wavelengths including an absorption wavelength of the measurement target component, and as illustrated in FIGS. 2 and 3, includes: a semiconductor laser element 2; a temperature detecting element 3 that detects the temperature of the semiconductor laser element 2; a cooling mechanism 4 that is mounted with the semiconductor laser element 2 and the temperature detecting element 3 and for cooling the semiconductor laser element 2; a sub-mount 5 provided between the semiconductor laser element 2 and temperature detecting element 3, and the cooling mechanism 4; and a hermetic container 6 that contains them.

The semiconductor laser element 2 is, for example, a distributed feedback laser (DFB laser) that emits the laser light X having infrared wavelengths, and in particular, in the present embodiment, a quantum cascade laser in which multiple well layers are connected in a cascaded manner and which emits light by optical transitions between subbands formed in the quantum wells.

The temperature detecting element 3 is one that detects the temperature of the semiconductor laser element 2 by detecting the temperature of the sub-mount 5 mounted with the semiconductor laser element 2. The temperature detecting element 3 in the present embodiment is a thermistor, and provided in the vicinity of the semiconductor laser element 2 in order to reduce the difference from the temperature of the semiconductor laser element 2. The temperature detecting element 3 in FIG. 2 is provided laterally to the semiconductor laser element 2, but may be provided in another position. In addition, by providing the temperature detecting element 3 oppositely to a rear end surface on the side opposite to the light emitting surface of the semiconductor laser element 2, light leaking out of the rear end surface of the semiconductor laser element 2 can be shielded to reduce stray light.

The cooling mechanism 4 is one configured using a Peltier element, and the upper surface thereof is adapted to be a heat absorption surface. In addition, the sub-mount 5 is provided in contact with the heat absorption surface. The cooling mechanism 4 is controlled by a control part COM having acquired the detected temperature by the temperature detecting element 3. Specifically, the control part COM uses the detected temperature by the temperature detecting element 3 to control electric power to be provided to the Peltier element and makes the detected temperature by the temperature detecting element 3 equal to a desired temperature.

The sub-mount 5 is a ceramic substrate made of, for example, aluminum nitride (AlN), silicon carbide (SiC), or the like. On the upper surface of the sub-mount 5, the semiconductor laser element 2 and the temperature detecting element 3 are provided. In addition, on the upper surface of the sub-mount 5, metal layers 51, 52, and 53 electrically connected to the respective elements 2 and 3 are formed.

The hermetic container 6 is one that forms a hermetic space such as a butterfly package, and a side wall facing the light emitting surface of the semiconductor laser element 2 is formed with a light lead-out part 61 for leading the laser light X to the outside. The light lead-out part 61 is provided with an optical window member 62, and the optical window member 62 is tilted slightly (e.g., at an angle of two degrees) so as to prevent the laser light X reflected by the optical window member 62 from returning to the semiconductor laser element 2 again.

Also, the hermetic container 6 is provided with output terminals T1 and T2 for outputting the output of the temperature detecting element 3 to the outside and feed terminals T3 and T4 for feeding power to the semiconductor laser element 2. Which of the temperature detecting element 3 and the semiconductor laser element 2 is connected to the output terminals T1 and T2 or the feed terminals T3 and T4 is arbitrarily determined. In addition, the hermetic container 6 is also provided, with feed terminals T5 and T6 for feeding power to the Peltier element of the cooling mechanism 4.

The output terminals T1 and T2 are connected with temperature detecting wires L1 and L2 electrically connected to the temperature detecting element 3. There are two output terminals T1 and T2, and one T1 of the output terminals is connected with the wire L1 connected to the metal layer 51 electrically connected to one electrode of the temperature detecting element 3, whereas the other output terminal T2 is connected with the wire L2 electrically connected to the other electrode of the temperature detecting element 3. These wires L1 and L2 are, for example, gold wires.

The feed terminals T3 and T4 for the semiconductor laser element 2 are connected with wires L3 and L4 for the semiconductor laser element 2, which are electrically connected to the semiconductor laser element 2. There are two feed terminals T3 and T4, and one T3 of the feed terminals is connected with the wire L3 connected to the metal layer 52 electrically connected to one electrode of the semiconductor laser element 2, whereas the other feed terminal T4 is connected with the wires L4 electrically connected to the other electrode of the semiconductor laser element 2 via the metal layer 53. Similarly, the Peltier element feed terminals T5 and T6 are connected with wires L5 and L6 for the Peltier element, which are electrically connected to the Peltier element.

Further, the semiconductor laser device 100 of the present embodiment includes a heat capacity increasing part 7 that is provided interposed between the temperature detecting element 3 and output terminal T1, and the output terminal T2, and contacts with at least part of the temperature detecting wires L1 and L2 to increase the heat capacity of the wire L1 or L2.

The heat capacity increasing part 7 is provided in contact with part of the wire L2 directly connecting the output terminal T2 and the temperature detecting element 3. The heat capacity increasing part 7 is one that reduces heat transfer from the output terminal T2 while keeping the electrical conduction of the wire L2. Specifically, the heat capacity increasing part 7 is configured of an insulating material, and the material desirably has flexibility because it covers the wire L2 and is flexible resin such as silicone. Also, the heat capacity increasing part 7 is provided so as to cover the periphery of part of the temperature detecting wire L2. Further, the heat capacity increasing part 7 is provided in contact with the sub-mount 5 as well.

In addition, the heat capacity increasing part 7 may be provided so as to cover at least part of the temperature detecting element 3 together with at least part of the temperature detecting wire L2. When silicone is used for the heat capacity increasing part 7, siloxane gas may be produced, and since the siloxane gas causes a failure in electronic equipment, such as a contact failure, the heat capacity increasing part 7 made of silicone is desirably decreased in its volume.

Effect of Present Embodiment

In such a semiconductor laser device 100, since there is provided the heat capacity increasing part 7 that contacts with the wire L2 connecting the temperature detecting element 3 and the Output terminal T2 to increase the heat capacity of the wire L2, the amount of heat transferring through the wire L2 and flowing into the temperature detecting element 3 can be reduced. As a result, the temperature of the semiconductor laser element 2 can be accurately detected by the temperature detecting element 3, and the temperature of the semiconductor laser element 2 can be highly accurately controlled. That is, the difference between the detected temperature by the temperature detecting element 3 and the temperature of the semiconductor laser element 2 can be reduced to highly accurately control the temperature of the semiconductor laser element 2. The gas analysis apparatus 10 using such a semiconductor laser device 100 is capable of suppressing variations in the oscillation wavelengths of the semiconductor laser element 2 and accurately analyzing the measurement target component contained in the gas.

Other Embodiments

Note that the present invention is not limited to the above-described embodiment.

Figure 4:
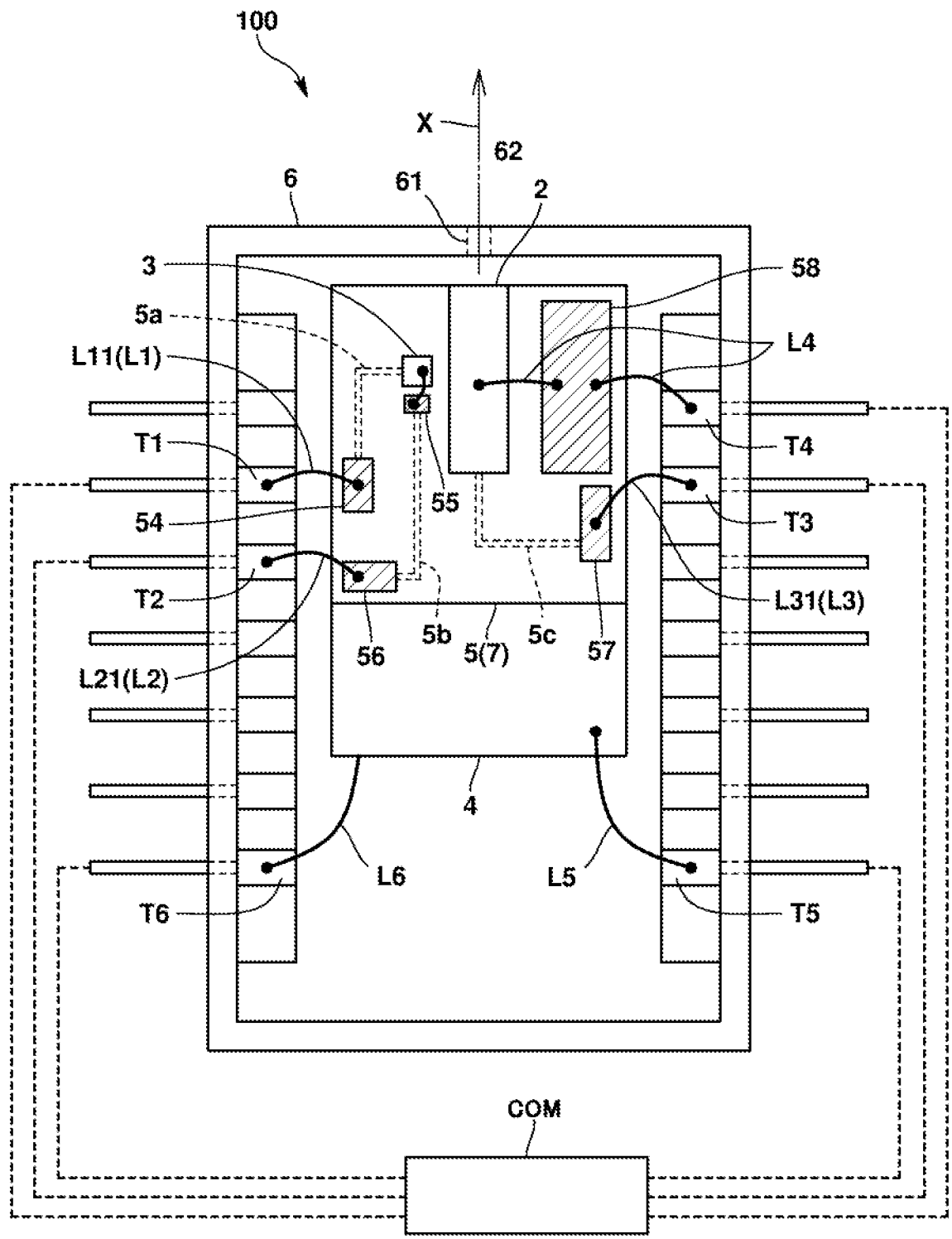
FIG. 4 is a plan view schematically illustrating the overall configuration of a semiconductor laser device according to a variation.
Figure 5:
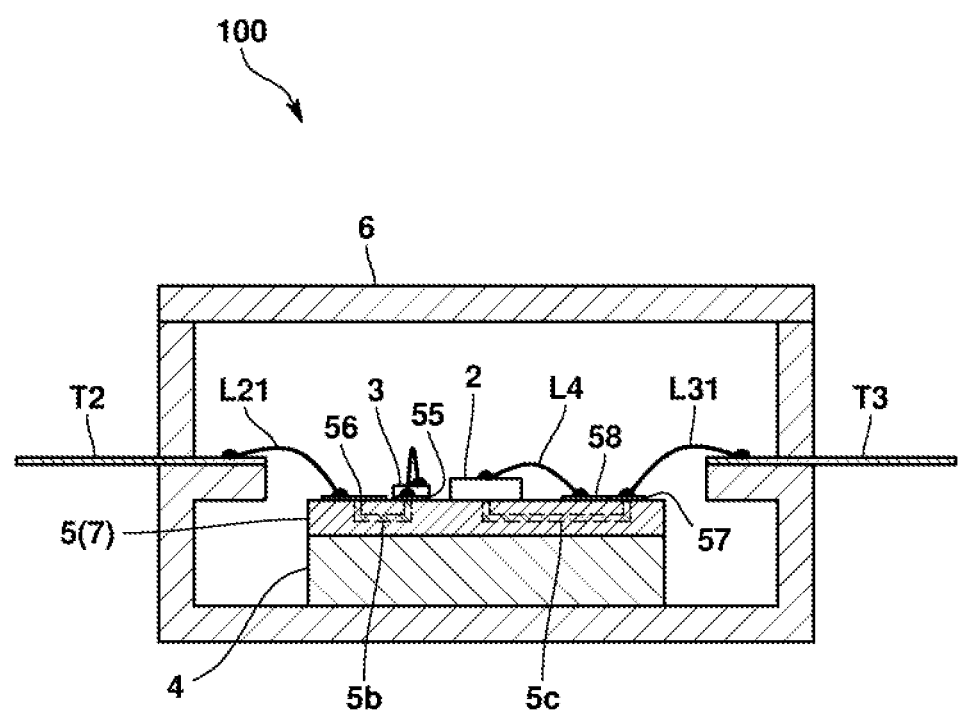
FIG. 5 is a cross-sectional view schematically illustrating the overall configuration of the semiconductor laser device according to the variation.

For example, the above-described embodiment is configured to connect the output terminals T1 and T2 and the temperature detecting element 3 via the wires L1 and L2 above the sub-mount 5, but as illustrated in FIGS. 4 and 5, may be configured to embed the temperature detecting wires L1 and L2 in the sub-mount 5. The sub-mount 5 illustrated in FIGS. 4 and 5 is configured of a multilayer ceramic substrate. In this configuration, the temperature detecting wires L1 and L2 are partly configured of wires 5a and 5b in the multilayer ceramic substrate.

Specifically, the one electrode of the temperature detecting element 3 is electrically connected to the wire 5a, and the wire 5a is electrically connected to a metal layer 54. Further, the metal layer 54 is electrically connected to the output terminal T1 by a lead wire L11 such as a gold wire. On the other hand, the other electrode of the temperature detecting element 3 is electrically connected to a metal layer 55 formed in the vicinity of the temperature detecting element 3, and the metal layer 55 is electrically connected to the wire 5b. Further, the wire 5b is electrically connected to a metal layer 56, and the metal layer 56 is electrically connected to the output terminal T2 by a lead wire L2 such as a gold wire.

As described, embedding parts of the temperature detecting wires L1 and L2 (in particular, the wire L2 connected to the other electrode of the temperature detecting element 3) allows the sub-mount 5 itself to function as a heat capacity increasing part 7, thus making it possible to reduce the amount of heat transferring through the wire L2 and flowing into the temperature detecting element 3.

Also, the one electrode of the semiconductor laser element 2 is electrically connected to a wire 5c in the multilayer ceramic substrate, and the wire 5c is electrically connected to a metal layer 57. Further, the metal layer 57 is electrically connected to the feed terminal T3 by a lead wire L31 such as a gold wire. On the other hand, the other electrode of the semiconductor laser element 2 is electrically connected to the feed terminal T4 by the wire L4 such as a gold wire via a metal layer 58. In addition, it is not required that the wires L3 and L4 for the semiconductor laser element 2 are configured to be embedded in the sub-mount.

As a configuration for embedding the wires L1 and L2 in the sub-mount 5, in addition to the configuration using the wires 5a and 5b in the multilayer ceramic substrate as described above, it may be configured to form grooves in the sub-mount 5, contain the wires L1 and L2 in the grooves, and seal them with resin or the like. Besides, the wires L1 and L2 may be laid in contact with the surface of the sub-mount 5.

Figure 6:
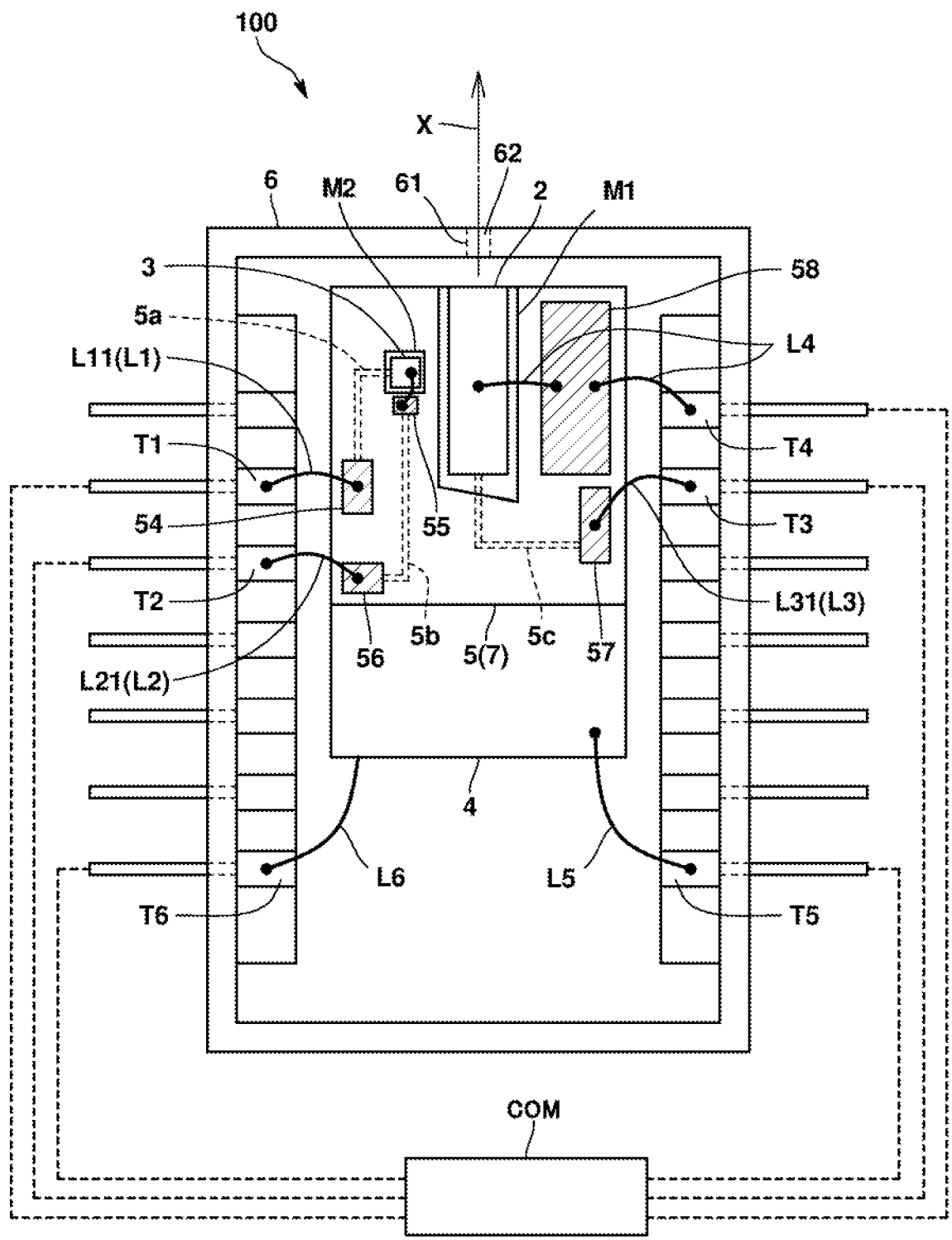
FIG. 6 is a plan view schematically illustrating the overall configuration of a semiconductor laser device according to a variation.
Figure 7:
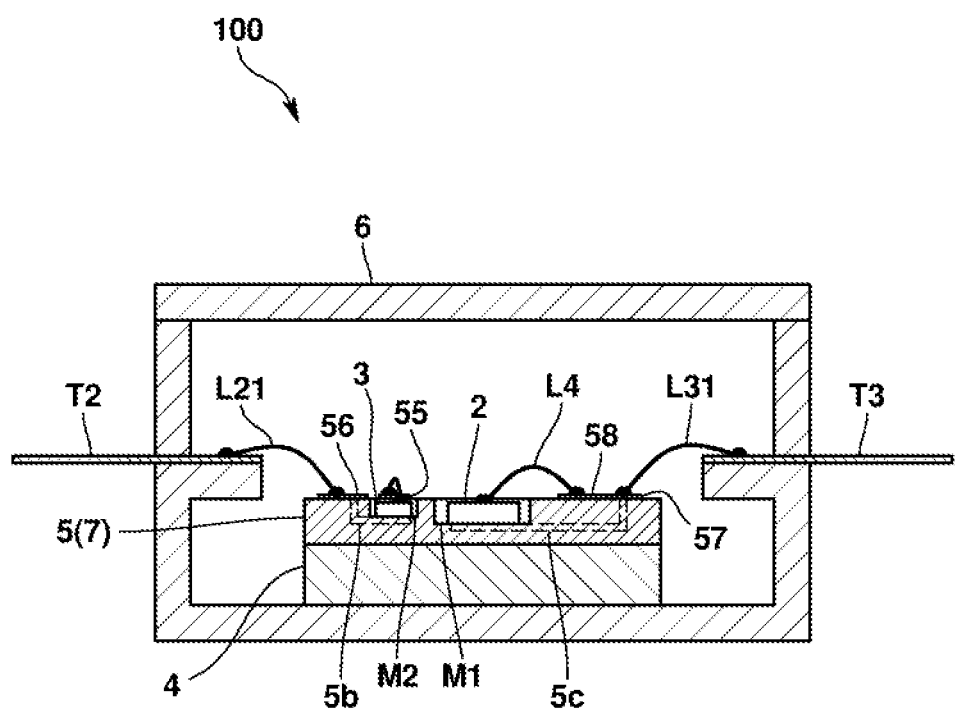
FIG. 7 is a cross-sectional view schematically illustrating the overall configuration of the semiconductor laser device according to the variation.

Also, as illustrated in FIGS. 6 and 7, the sub-mount 5 may be formed with a recess part M1 for containing the semiconductor laser element 2 and formed with a recess part M2 for containing the temperature detecting element 3. In this case, the inner surface of the recess part M1 faces the rear end surface of the semiconductor laser element and functions as a light shielding part that shields the light leaking out of the rear end surface to reduce stray light. Also, the light shielding surface of the light shielding surface is tilted slightly (e.g., at an angle of two degrees) so as to prevent reflected light from returning to the semiconductor laser element 2 again. In addition, in FIGS. 6 and 7, the sub-mount 5 is configured of the multilayer ceramic substrate, but may be configured of a simple ceramic substrate.

Further, a step part may be formed facing the rear end surface of the semiconductor laser element 2. The height dimension of the step part is desirably made higher than the height dimension of the semiconductor laser element 2, and desirably made equal to or higher than, for example, 2 mm.

In the above-described embodiment, described is the semiconductor laser device having the quantum cascade laser element; however, the semiconductor laser device may be one having another semiconductor laser element (e.g., a distributed Bragg-reflector laser (DBP laser)).

A method for driving the semiconductor laser element 2 may be a continuous oscillation (CW) method, a pseudo-continuous oscillation (pseudo-CW) method, or a pulse oscillation method.

In the above-described embodiment, described is an example of applying the semiconductor laser device to the gas analysis apparatus; however, the semiconductor laser device may be applied to another optical analysis apparatus.

Also, the analysis apparatus using the semiconductor laser device in the above-described embodiment may be one that, for example, in addition to being used to analyze the exhaust gas of a vehicle, analyzes a measurement target component (e.g., $CO$, $CO_2$, $H_2O$, $NO$, $NO_2$, $N_2O$, $NH_8$, a hydrocarbon component such as HC, or an oxygen-containing hydrocarbon component such as HCHO) in various gases (e.g., environmental gas) such as the atmosphere, or analyze liquid.

Besides, it should be appreciated that the present invention is not limited to the above-described embodiment, but can be variously modified without departing from the scope thereof.

REFERENCE SIGNS LIST

100: Semiconductor laser device
2: Semiconductor laser element
3: Temperature detecting element
T1, T2: Output terminal
L1, L2: Wire
7: Heat capacity increasing part
4: Cooling mechanism
COM: Control part
5: Sub-mount
5a, 5b: Wire in multilayer ceramic substrate

The invention claimed is:
1. A semiconductor laser device used for optical analysis, the semiconductor laser device comprising:
 a semiconductor laser element that is a quantum cascade laser;
 a temperature detecting element that detects temperature of the semiconductor laser element;
 a multilayer ceramic substrate that is a single substrate having an upper surface that includes metal layers and a bottom surface facing in opposite directions, wherein the semiconductor laser element and the temperature detecting element are affixed to the upper surface of the multilayer ceramic substrate by direct attachment to the metal layers;
 a Peltier element that physically contacts the bottom surface of the multilayer ceramic substrate and controls the temperature of the semiconductor laser element;
 an output terminal that outputs an output of the temperature detecting element to an outside;
 wiring that electrically connects the temperature detecting element and the output terminal; and
 a heat capacity increasing part that is interposed between the temperature detecting element and the output terminal to increase heat capacity of the wiring and is configured by the multilayer ceramic substrate by embedding at least part of the wiring in the multilayer ceramic substrate.
2. The semiconductor laser device according to claim 1, further comprising:

a control part that uses detected temperature by the temperature detecting element to control the Peltier element.

3. The semiconductor laser device according to claim 1, further comprising:
a light shielding part that faces an end surface on a side opposite to a light emitting surface of the semiconductor laser element to shield light coming out of the end surface.

4. The semiconductor laser device according to claim 1, wherein
the temperature detecting element is provided facing an end surface on a side opposite to a light emitting surface of the semiconductor laser element.

5. An analysis apparatus that analyzes a measurement target component contained in fluid, the analysis apparatus comprising:
a measurement cell into which the fluid is introduced;
the semiconductor laser device according to claim 1 that irradiates the measurement cell with laser light;
a light detector that detects laser light passing through the measurement cell; and
an analysis part that uses a detected signal by the light detector to analyze the measurement target component.

* * * * *